(12) United States Patent
Oldham et al.

(10) Patent No.: US 11,215,805 B2
(45) Date of Patent: Jan. 4, 2022

(54) MULTI-PHOTON ENDOMICROSCOPE FOR VERTICAL CROSS-SECTIONAL IMAGING

(71) Applicant: THE REGENTS OF THE UNIVERSITY OF MICHIGAN, Ann Arbor, MI (US)

(72) Inventors: Kenn Oldham, Ann Arbor, MI (US); Jongsoo Choi, Stoneham, MA (US); Xiyu Duan, Ann Arbor, MI (US); Thomas D. Wang, Ann Arbor, MI (US); Haijun Li, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 169 days.

(21) Appl. No.: 16/465,558

(22) PCT Filed: Dec. 4, 2017

(86) PCT No.: PCT/US2017/064539
§ 371 (c)(1),
(2) Date: May 30, 2019

(87) PCT Pub. No.: WO2018/102822
PCT Pub. Date: Jun. 7, 2018

(65) Prior Publication Data
US 2020/0096753 A1    Mar. 26, 2020

Related U.S. Application Data

(60) Provisional application No. 62/429,438, filed on Dec. 2, 2016.

(51) Int. Cl.
*G02B 26/08* (2006.01)
*G02B 21/00* (2006.01)
(Continued)

(52) U.S. Cl.
CPC ...... *G02B 21/0048* (2013.01); *A61B 1/00172* (2013.01); *A61B 1/063* (2013.01); *G02B 26/101* (2013.01)

(58) Field of Classification Search
CPC .............. G02B 21/0048; G02B 26/101; G02B 23/2469; G02B 23/2476; G02B 21/0076;
(Continued)

(56) References Cited

U.S. PATENT DOCUMENTS

| 4,478,482 A | 10/1984 | Koester |
| 6,157,448 A * | 12/2000 | Kowa ...................... G01J 4/00 356/365 |

(Continued)

OTHER PUBLICATIONS

International Search Report and Written Opinion from International Application No. PCT/US2017/065439 dated Apr. 13, 2018.

*Primary Examiner* — Euncha P Cherry
(74) *Attorney, Agent, or Firm* — Marshall, Gerstein & Borun LLP

(57) ABSTRACT

A multi-photon optical probe includes a probe housing, a lateral scanning stage coupled to a lateral mirror assembly and a remote axial scanning stage coupled to an axial mirror assembly. The lateral scanning stage is adapted to scan output laser energy over a planar scan area of the sample by moving the lateral mirror assembly. The axial scanning stage is adapted to scan the output laser energy over a vertical depth range of the sample, which, combined with the planar scan area, forms a 3-dimensional volume. A controller operates in conjunction with a number of remote actuating legs coupled to the axial mirror assembly in order to provide level imaging plane which in turn provides for a clear scanned image.

18 Claims, 14 Drawing Sheets

(51) Int. Cl.
*A61B 1/00* (2006.01)
*A61B 1/06* (2006.01)
*G02B 26/10* (2006.01)

(58) Field of Classification Search
CPC ... G02B 21/002; A61B 1/00172; A61B 1/063; G01N 21/6458
USPC .................................................... 359/201.2
See application file for complete search history.

(56) References Cited

U.S. PATENT DOCUMENTS

| | | |
|---|---|---|
| 2008/0080060 A1 | 4/2008 | Messerschmidt |
| 2011/0125029 A1* | 5/2011 | Wang ................. G02B 26/0841 600/476 |
| 2014/0111703 A1 | 4/2014 | Luff |
| 2014/0255985 A1 | 9/2014 | Oldham et al. |

* cited by examiner

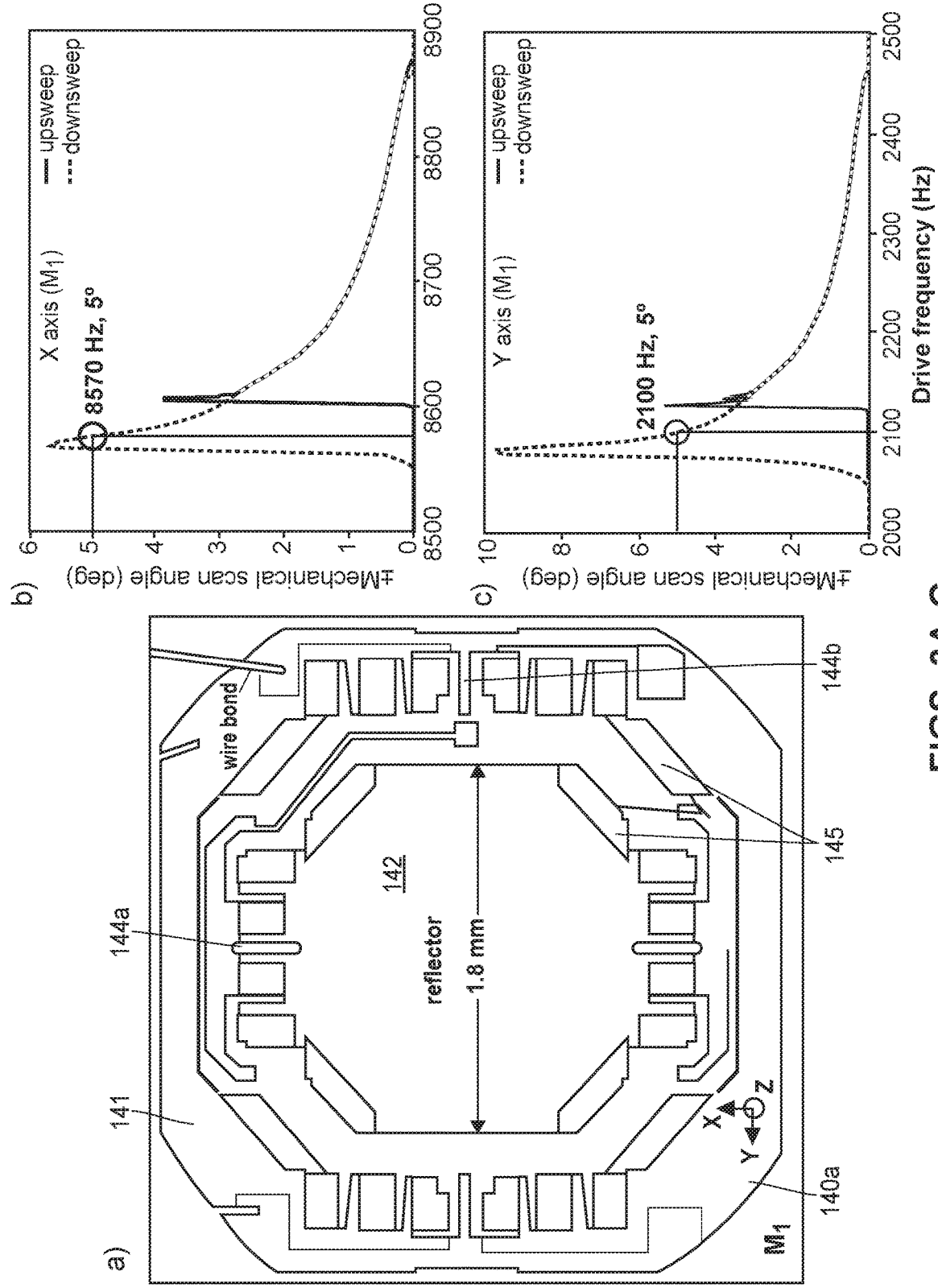
FIGS. 3A-C

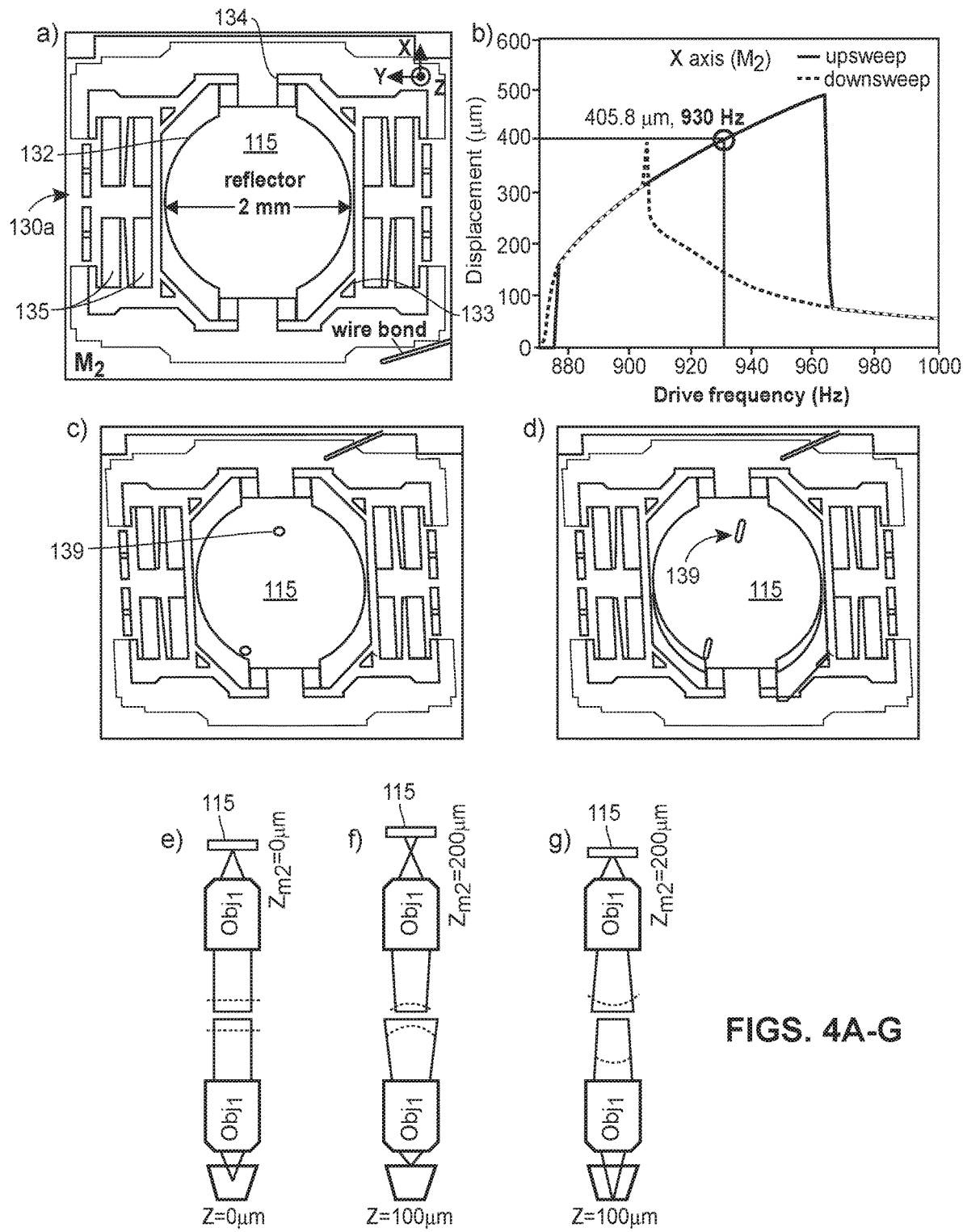
FIGS. 4A-G

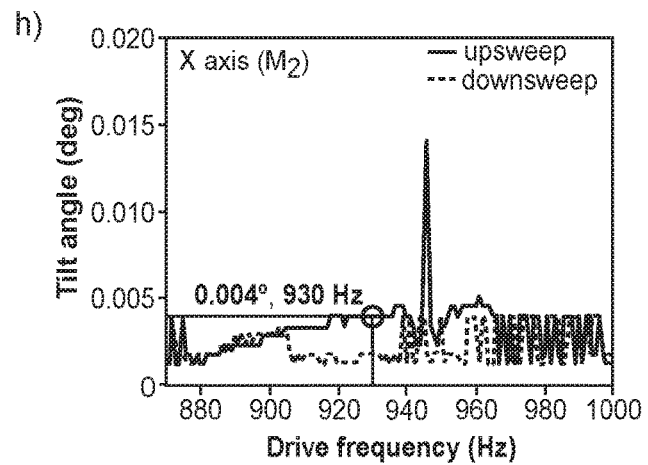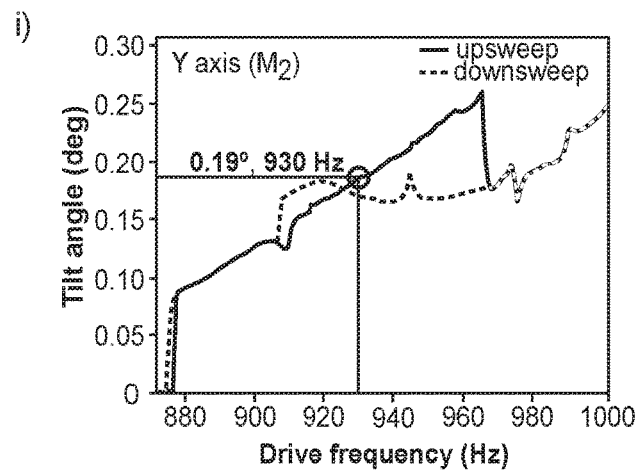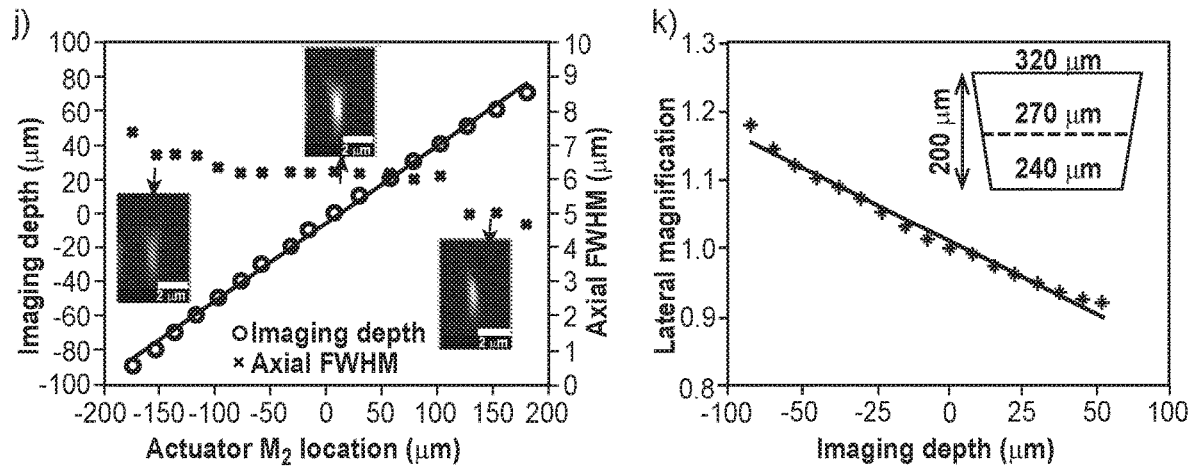
FIGS. 4H-K

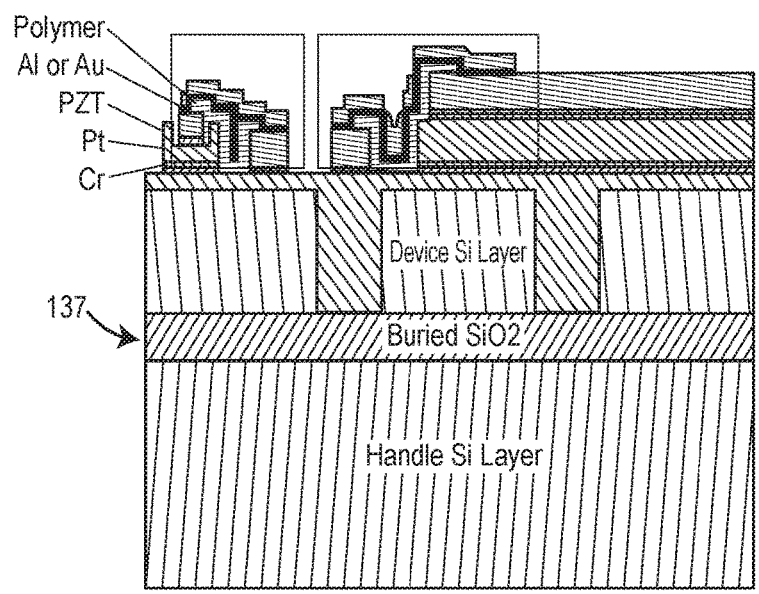
FIG. 10
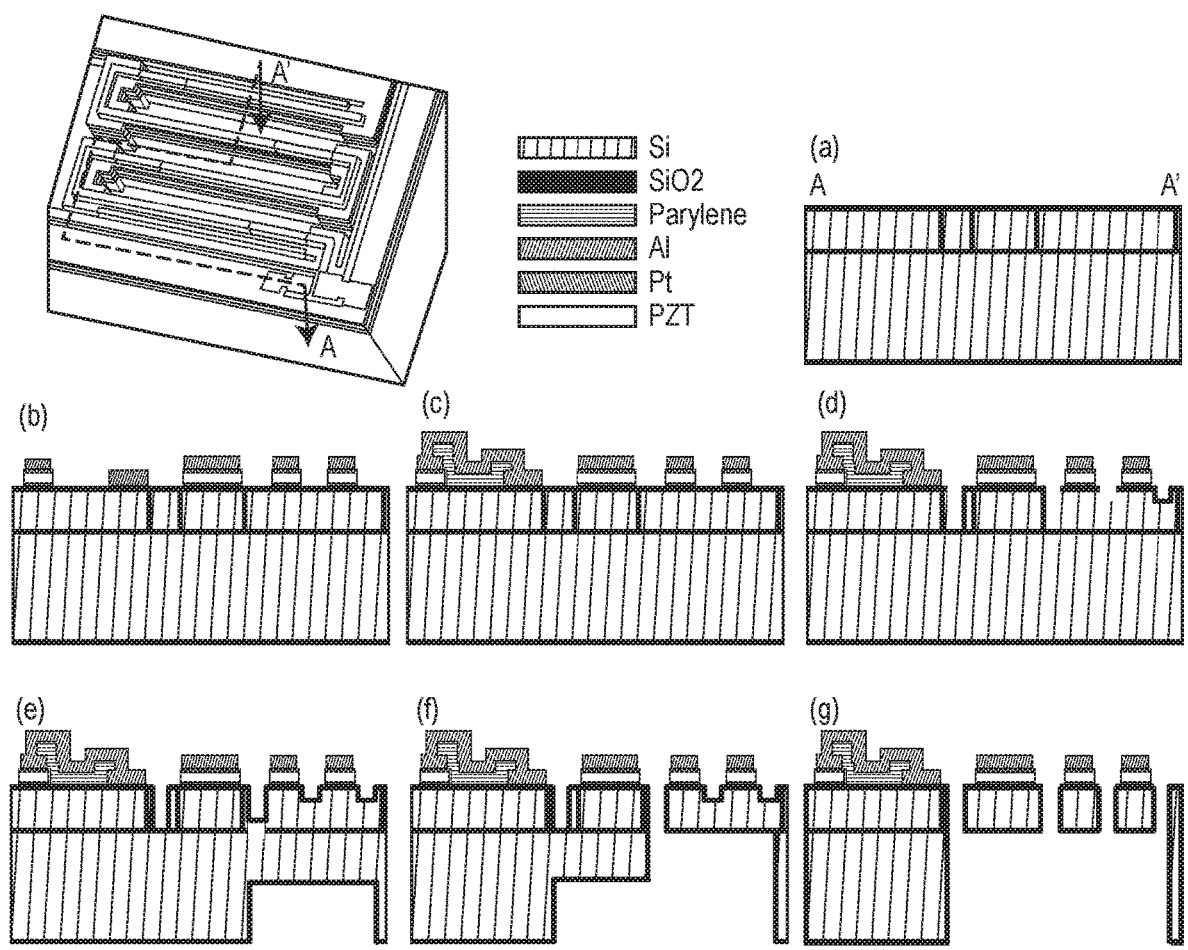
FIGS. 11A-G

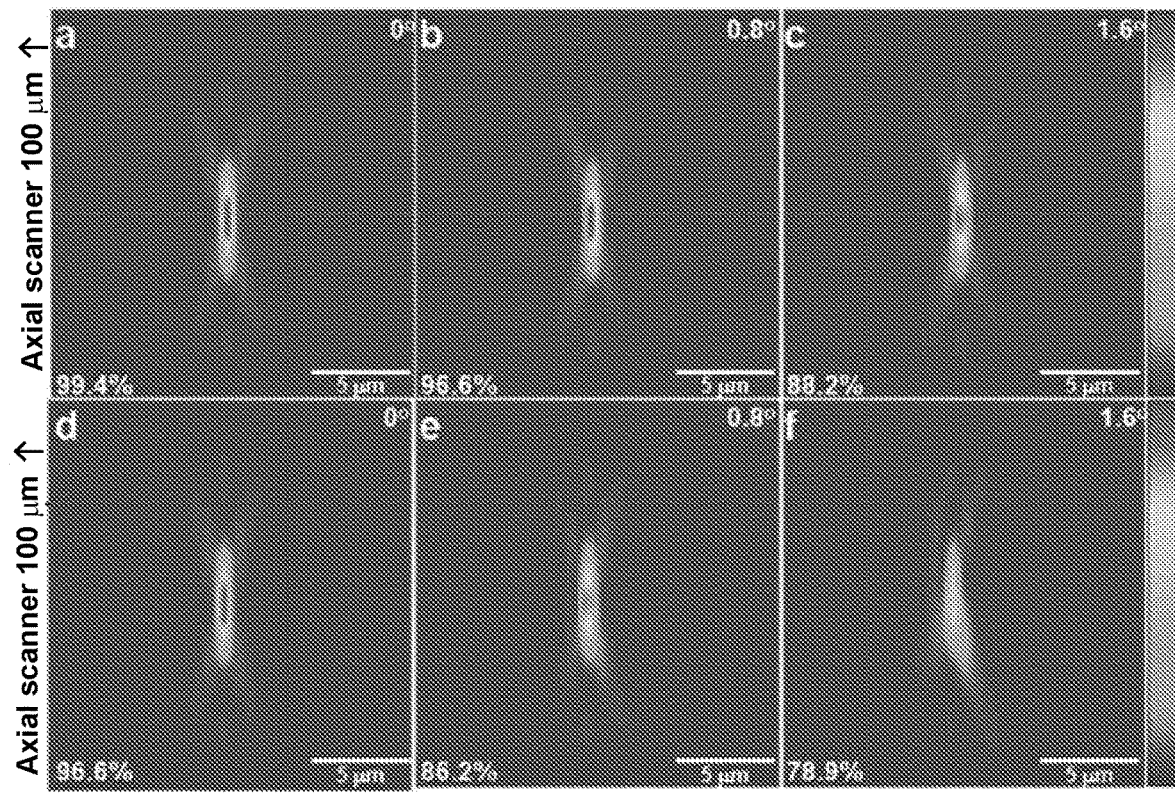
FIGS. 12A-F
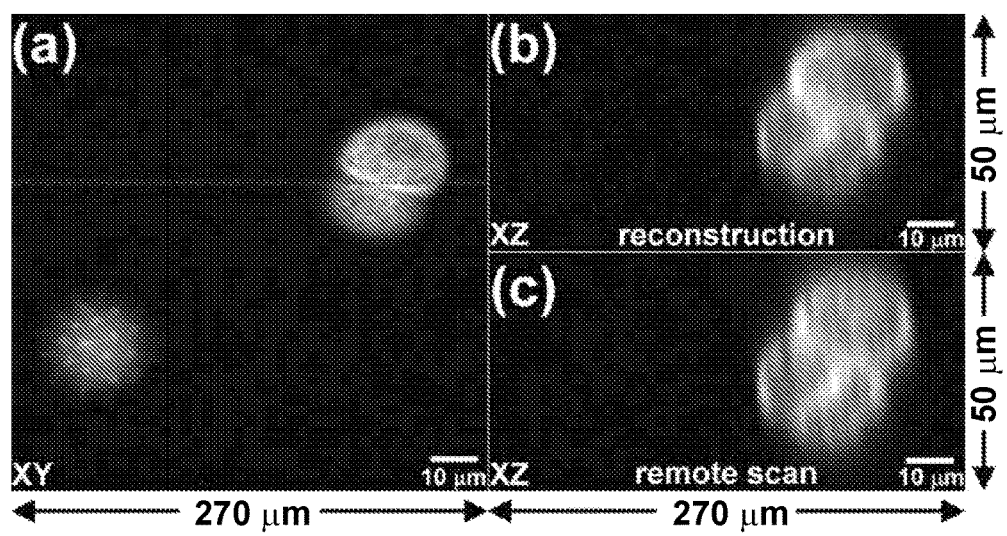
FIGS. 13A-C

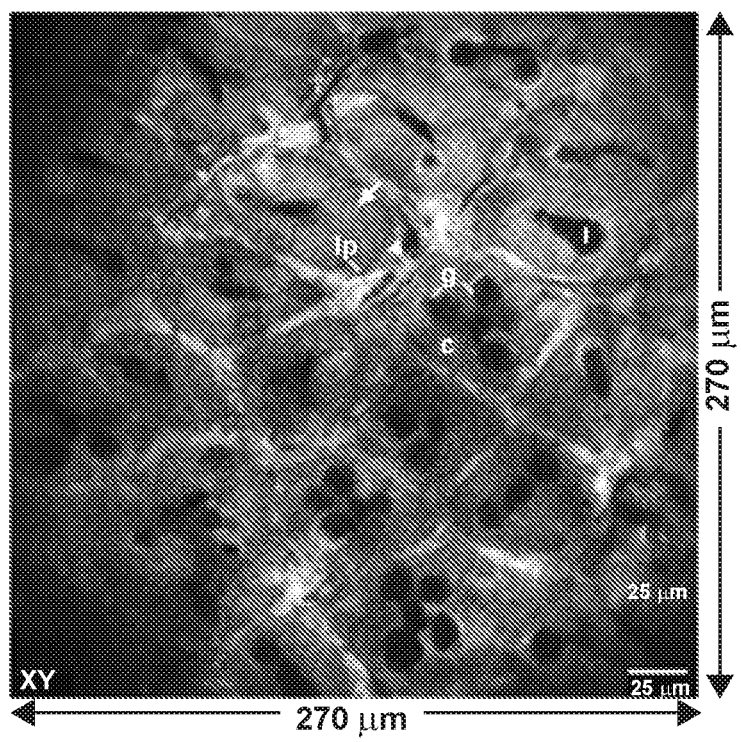
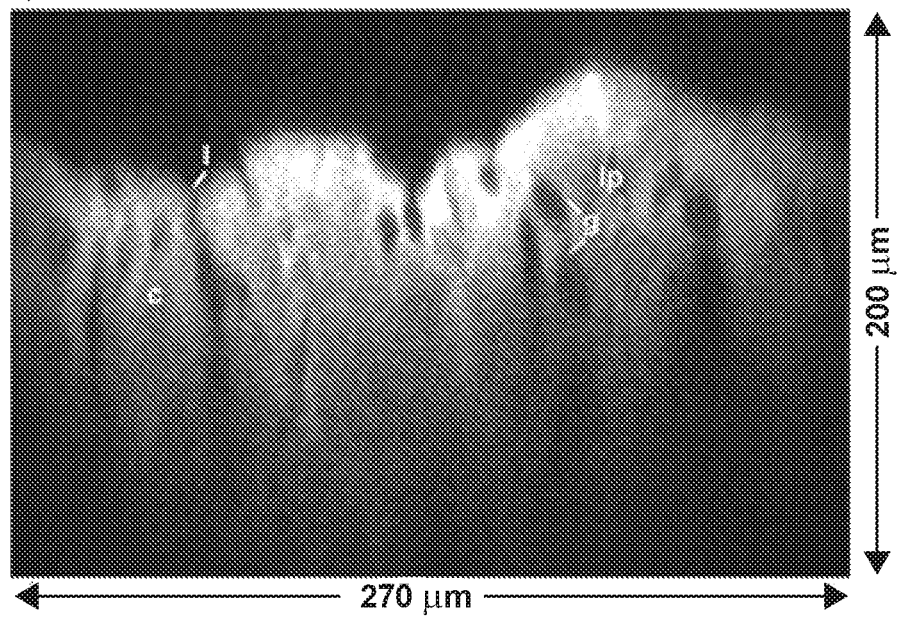
FIGS. 14A,B

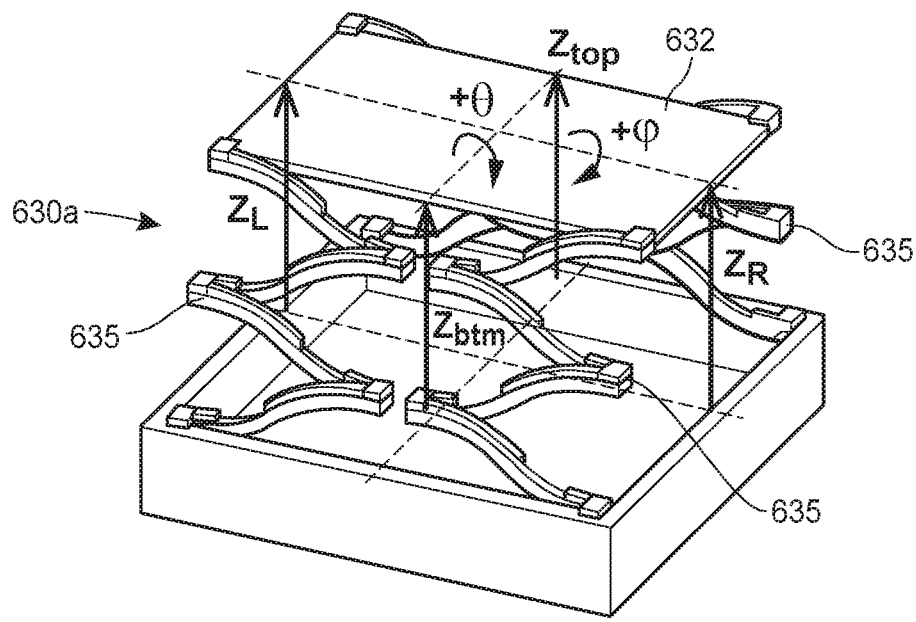
FIG. 15
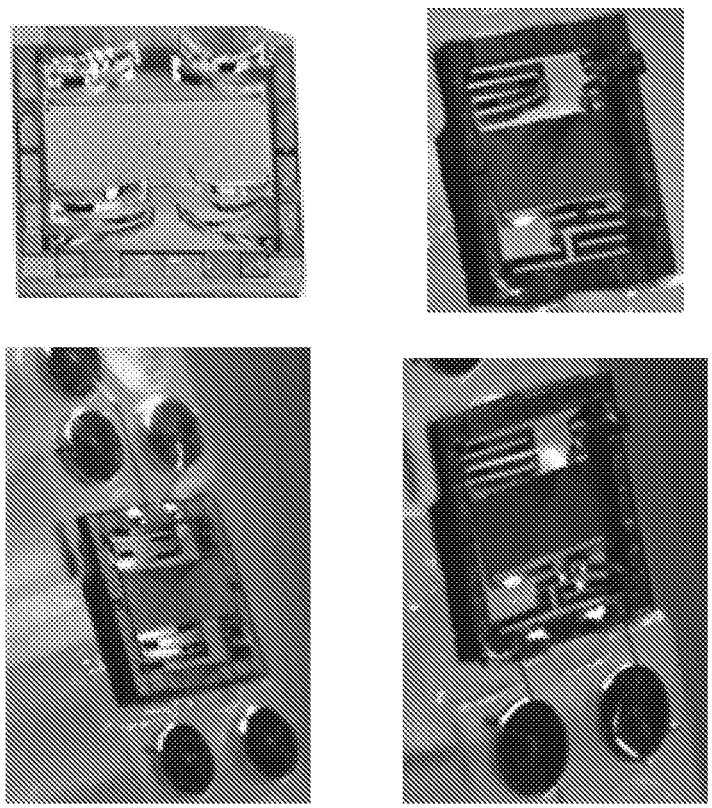
FIGS. 16A-D

MULTI-PHOTON ENDOMICROSCOPE FOR VERTICAL CROSS-SECTIONAL IMAGING

CROSS-REFERENCE TO RELATED APPLICATION

This application claims priority to U.S. Provisional Application No. 62/429,438, entitled "Vertical Beam Scanning In Multi-Photon Endomicroscopy with Remote MEMS Scanning Mechanisms", and filed Dec. 2, 2016, which is incorporated herein by reference in its entirety.

STATEMENT OF GOVERNMENT SUPPORT

This invention was made with government support under grants EB020644 and CA142750 awarded by the National Institutes of Health. The government has certain rights in the invention.

FIELD OF THE DISCLOSURE

The present disclosure generally relates to techniques for imaging tissue using an optical instrument and, more particularly, to techniques for allowing two-dimensional (2D) and three-dimensional (3D) scanning using an optical instrument.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Endomicroscopes are typically used to scan objects in a horizontal plane, parallel to a surface of a tissue. However, a vertical plane (also referred to herein as an axial plane or an into-tissue plane) can be more useful for imaging biological processes that develop perpendicular to the tissue surface, processes such as normal epithelial development, stem cell migration, and tumor invasion. The desire to image the vertical plane of in vivo biological processes has motivated the development of a number of designs for miniature instruments including multi-photon microscopy devices. However, none of the previous designs provide for axial displacement and scan speed needed to generate real-time cross-sectional images, and none of the previous designs do so in a useful form factor that does not seriously harm the specimen. Conventional endomicroscopes, for example, are bulky and cannot repetitively pass into regions to be imaged such as the colon.

Multi-photon microscopy offers both high resolution and significant imaging depth using intense pulses of long wavelength light that are capable of penetrating beneath the image surface to excite shorter wavelength photons via nonlinear effects. Relative to other deep tissue optical imaging modalities, multi-photon microscopy has benefits of reduced photobleaching and capacity to excite endogenous fluorescence in addition to its compatibility with a variety of targeted fluorescent biomarkers.

Despite a number of miniature multi-photon instruments, there is a need for endomicroscopes that can image deep into tissue with axial beam scanning. Existing systems capable of deep imaging utilize conventional bench top microscopes and thus increase experimental complexity, study invasiveness, and biological behavior.

To best make use of multi-photon imaging capabilities in a small instrument, it is desirable to support fast axial (i.e., vertical or into-tissue) scanning of an ultrafast laser. Sufficiently fast axial scanning can support in vivo vertical optical sectioning, thereby providing real-time cross-sectional images of tissue in the same plane that is used by histologists to diagnose and monitor diseases such as colon or esophageal cancer. However, previous endoscopic instruments have provided limited support for altering depth-of-focus during multi-photon imaging. Several en face multi-photon endoscopes have characterized out-of-plane, or z-axis, resolution, but only by physically moving the sample being imaged. When moving in the z-axis, it is of particular importance to maintain a level imaging plane in order to provide for a clear image.

To create an image in the vertical plane, a series of horizontal plane images are acquired and then reconstructed. This approach is usually slow and difficult to accomplish, as vibrations in the sample may cause motion artifacts.

Existing scanning systems oftentimes generate axial movement of an optical lens assembly using a number of large actuators which require large distal optics (e.g., 5-10 mm). These systems may employ Lissajous, or "in-plane" scanning in the axial direction where the imaging device must move to a desired depth, stop, scan the tissue, then travel to the next desired depth and repeat this process. In dual-axis confocal microscopy, piezoelectric actuation may be employed and also may use selectable Lissajous scanning between the X-Y and X-Z planes. In systems having Raster, or "out of plane" scanning capabilities, imaging is only possible in the X-Z plane. These systems also require large distal optics.

SUMMARY

The present application describes a handheld optical device that may be used as a microscope system for real-time, 3D optical imaging. Systems for a multi-photon endomicroscope utilize miniature vertical actuators to provide for fast axial scanning in addition to large axial (i.e., vertical) displacement using miniaturized equipment. Vertical actuation is obtained using both electrostatic and thin-film piezoelectric actuators in conjunction with multi-photon imaging modalities. Axial scanning is achieved based on electrostatic actuation and parametric resonance that can achieve high speed and large displacement scanning. Moreover, this axial scanning (i.e., along the Z-axis) is combinable with a lateral scanning, also based on electrostatic actuation and parametric resonance, that is able to scan a beam above different planar axes (i.e., the X-axis and the Y-axis). Moreover still, this lateral scanning can be achieved at different axial scanning depths, without changes in scan performance. The use of different resonant modes for the axial scanner from that of the lateral scanner further allows for better isolated control of scanning in different directions.

Multi-photon imaging offers a number of benefits for real-time, in vivo imaging of the epithelium and other regions compared to confocal imaging. For example, multi-photon imaging can provide greater image depth, less photo bleaching for longer term imaging studies, and can also provide for increased image resolution or reduced scattering. While dual axes confocal microscopy has shown potential for comparable imaging depth and resolution with vertical sectioning, larger instrument diameters are required for equivalent depth due to the need to provide light paths at off-axis angles. Because a single excitation wavelength can excite multiple fluorophores, multiplexing is substantially easier with multi-photon imaging than in other imaging modalities such as magnetic resonance imaging (MRI) and positron emission tomography (PET). Further, multi-photon excitation produces reduced photo damage and out-of-plane photo bleaching than other techniques. Multi-photon systems use a single optical path for both incident and returning light (though the path may be split off for collection purposes), and accordingly, as compared to dual axes imaging systems, use a round mirror geometry (as opposed to a generally dogbone geometry used by dual axes). Further, the lens arrangement in dual-axes systems require precise alignment of two collimating lenses using a mechanism such as a parabolic fixed mirror to ensure the separate beam paths align at the same point. Multi-photon arrangements do not have this alignment issue, though these systems require an appropriate relay lens configuration to map changes in axial displacement of the scanning mirrors to displacement of the focal point in tissue. One advantage of the present techniques is that imaging can occur without the need of fluorescent markers using endogenous fluorescence of tissues and/or cells.

The systems of the present application provide for real-time, axial or vertical scanning into the tissue, using mirror scanning approaches. This axial movement of the mirrors may be performed using thin-film piezoelectric and/or electrostatic actuators, which can provide substantial displacement (e.g., approximately 500 microns) while still having a small diameter (e.g., approximately 3 mm). Thin-film piezoelectric actuators can create larger axial translation at lower operating voltages as well as the ability to individually address actuating legs to compensate for non-uniform motion. Electrostatic actuators are relatively simple to fabricate and function at higher operating speeds. Additionally, if the mirror surface is built monolithically (i.e., as a single component), the device will have better initial uniformity.

The present multi-photon imaging system uses a two-photon effect, which occurs when two lower energy (i.e., longer wavelength) photons arrive at a biomolecule simultaneously to excite fluorescence. The probability of absorbing two photons increases with the square of intensity; thus, a high numerical aperture objective in the single axis configuration is used to maximize the intensity at the focus. Because of this physical principle, there is less sensitivity to tissue scattering and reduced photobleaching when compared to single photon fluorescence. Additionally, the longer excitation wavelengths used provides deeper tissue penetration.

In accordance with an example, a multi-photon optical probe includes a probe housing, a lateral scanning stage coupled to a lateral mirror assembly and at least partially being disposed in the probe housing, and an axial scanning stage coupled to an axial mirror assembly and at least partially being disposed in the probe housing. The probe housing has a proximal end and a distal end positioned at a sample and is adapted to produce an output laser energy. The lateral scanning stage is adapted to scan the output laser energy over a planar scan area of the sample by moving the lateral mirror assembly. The axial scanning stage is adapted to scan the output laser energy over a depth range of the sample. The depth range and the planar scan area form a 3-dimensional volume. The axial scanning stage includes a plurality of actuating legs positioned axially about the axial mirror assembly.

In some examples, an axial scanning stage for a multi-photon optical probe includes a frame, a mirror platform coupled to the frame, a plurality of actuator legs coupled to the frame and the mirror platform, and a plurality of electrical connectors positioned about the mirror platform. The mirror platform is adapted to support a mirror element. The actuator legs are adapted to raise the mirror platform along a vertical axis. The actuator legs and the electrical connectors are positioned axially about the mirror platform.

BRIEF DESCRIPTION OF THE DRAWINGS

For a more complete understanding of the disclosure, reference should be made to the following detailed description and accompanying drawing figures, in which like reference numerals identify like elements in the figures, and in which:

FIGS. 3A-3C illustrate top plan views of an example lateral scanning unit (FIG. 3A) and frequency response graphs (FIGS. 3B and 3C) depicting mechanical scan angles greater than 5.5 degrees for the inner and outer axes, respectively in accordance with various embodiments;

FIGS. 4A-4K are top plan views of an example axial scanning unit (FIG. 4A), a frequency response graph illustrating vertical displacement (FIG. 4B), and the unit characterized under a laser displacement sensor showing the laser beam spot at a resting state and resonating at 440 Hz (FIGS. 4C and 4D), illustrations of variances in the wavefront upon moving the axial actuators (FIGS. 4E-4G), tilt angles of the X axis (FIG. 4H and the Y axis (FIG. 4I) upon translating the axial actuators, a graph depicting the linear relationship between the position of the axial scanning mirror and the depth of the focal plane (FIG. J), and a graph depicting lateral magnification ranges over varying imaging depths, whereby the axial scanning unit uses resonant electrostatic actuators to provide axial movement, in accordance with various embodiments;

FIG. 10 is a cross-sectional view of an example actuator illustrating metal being placed over parylene bridges to and from a PZT layer to improve electrical reliability in accordance with various embodiments;

FIGS. 11A-G are fabrication illustrations of the actuator of FIG. 10 of an axial MEMS scanner in accordance with various embodiments;

FIGS. 12A-F are results of a point spread function for varying upward and downward displacements in accordance with various embodiments;

FIGS. 13A-C are images of pollen grains using combinations of the lateral and axial scanning units using electrostatic actuation systems in accordance with various embodiments;

FIGS. 14A and B are images of sample subject tissue using solely the lateral scanning unit and a combination of the lateral and electrostatic actuating axial scanning units in accordance with various embodiments;

FIG. 15 is a perspective view of an alternative design for an axial MEMS scanner in accordance with various embodiments;

FIGS. 16A-D illustrate completed piezoelectric vertical actuators, both before and after installation in a 3D-printed fixture for assembly to an imaging system in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, an optical instrument has an actuator mechanism that offers high image resolution and that can quickly scan deep into a tissue to create volumetric images. The optical components of the instrument may be sized small enough to easily move about and be manipulated in desired tissue. By using piezoelectric actuation, low-profile scanning devices can achieve large, high-speed displacement of optical components (e.g., mirrors) via microactuation, which allows for real-time cross-sectional and/or 3D images of tissue.

Multi-photon imaging can provide several benefits over dual axis imaging systems. For example, specimens require less photo bleaching because fluorescence is only generated where two or more incoming photons strike a molecule at the same time. Additionally, multi-photon imaging provides the ability to generate endogenous fluorescence from a variety of cell types, whereas dual axes imaging systems can only be performed using fluorescent molecule-labeled biomarkers. Multi-photon imaging also provides increased image resolution as well as opportunities for laser surgery using the high intensity ultrafast laser which is not possible with dual axes systems. Using multi-photon imaging systems requires a new optical design that can use actuator displacement to achieve axial scanning into a tissue. Multi-photon scanning design places stricter constraints on uniformity of the scanning motion when compared to dual axis scanning, thus the actuator design and configuration should be carefully considered.

Figure 1A:
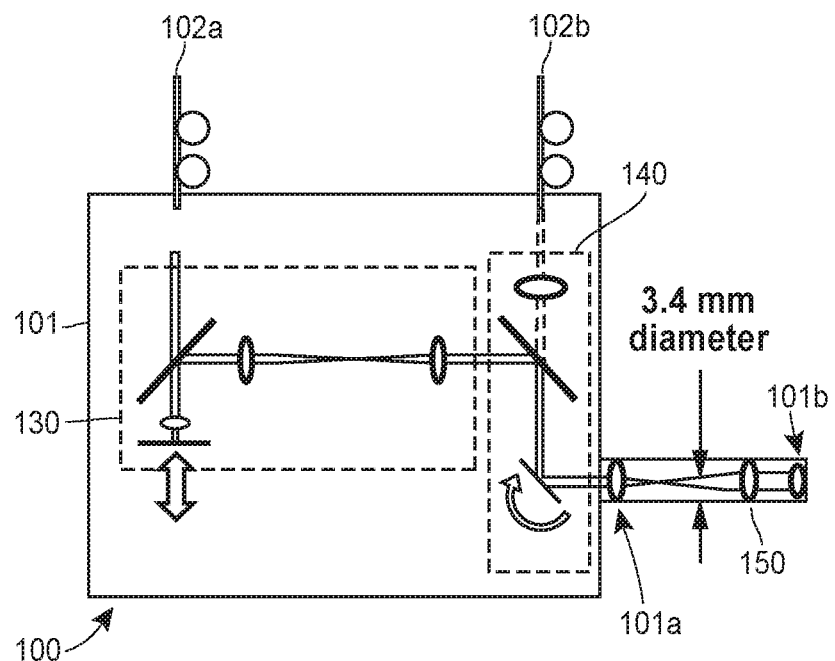
FIG. 1A is a schematic view of an optical probe having an axial scanning unit, a lateral scanning unit, and distal optics.
Figure 1B:
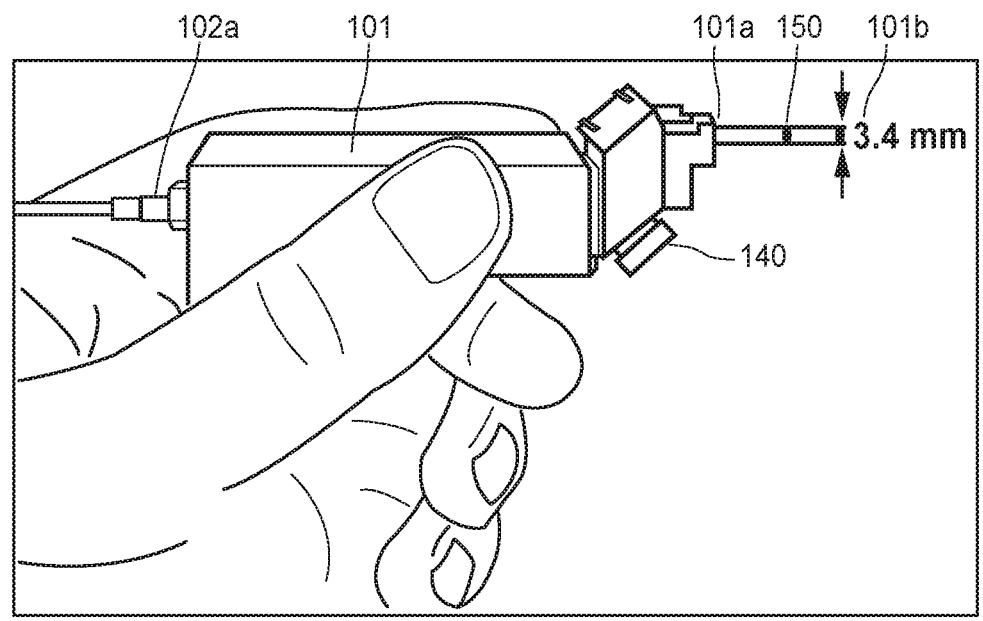
FIG. 1B is an illustration of an example multi-photon optical probe having the axial and lateral scanning units and distal optics in accordance with various embodiments.

As illustrated in FIGS. 1A and 1B, a multi-photon optical probe 100 includes an axial microelectromechanical system (MEMS) scanning unit or stage 130, a lateral (MEMS) scanning unit or stage 140, and distal optics 150. The lateral scanning unit 140 is adapted to scan the output laser energy over a planar scan area of the sample 103 by moving a lateral mirror assembly, and the axial scanning unit 130 is coupled to an axial mirror assembly and is adapted to scan the output laser energy over a depth range of the sample. The depth range and the planar scan area combine to form a three dimensional volume. As will be discussed, the axial scanning unit includes any number of actuating legs positioned axially about the axial mirror assembly. The axial scanning unit 130, lateral scanning unit 140, and distal optics 150 are all optically coupled to laser and light collection electronics (such as any number of multi-mode fibers, photomultiplier tubes, etc., not shown) via fiber optic cables 102a, 102b. Any number of these components can be at least partially disposed in a single, handheld probe housing frame 101. The probe housing frame 101 can include a proximal end 101a and a distal end 101b positioned at a sample 103 and is adapted to produce an output laser energy.

Figure 2:
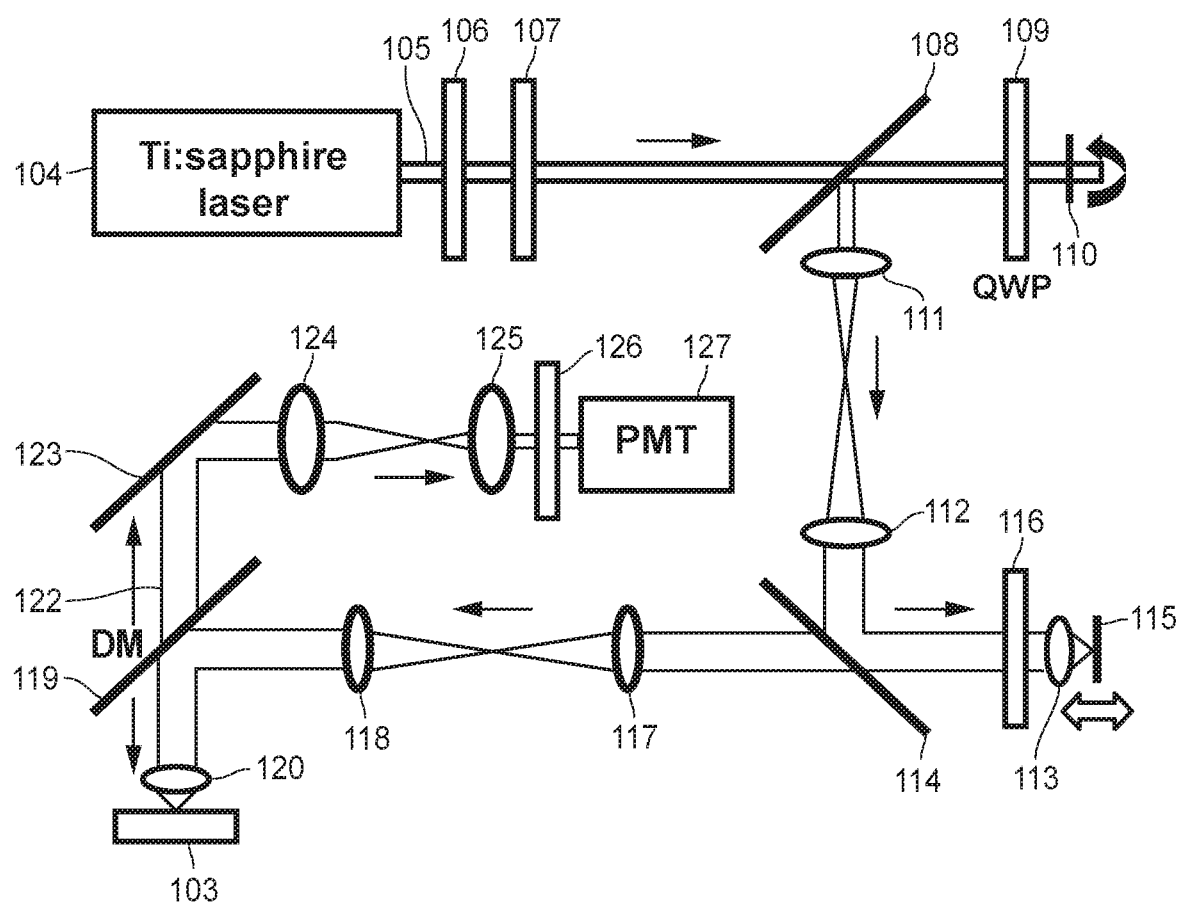
FIG. 2 is a schematic view of the optical probe of FIG. 1 in accordance with various embodiments.
Figure 5:
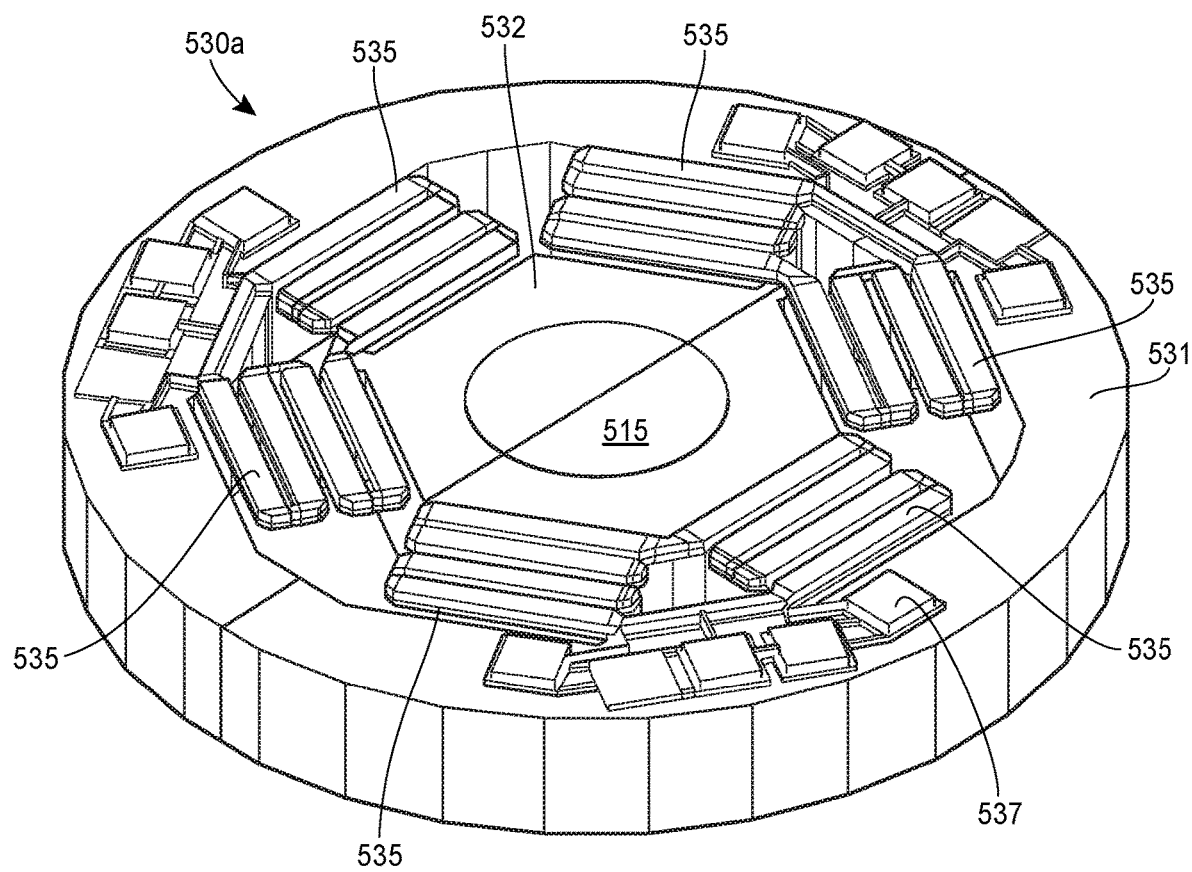
FIG. 5 is a perspective view of an example axial scanning actuator using thin-film piezoelectric actuators arranged about a mirror platform in an axial or circular form factor in accordance with various embodiments.
Figure 6:
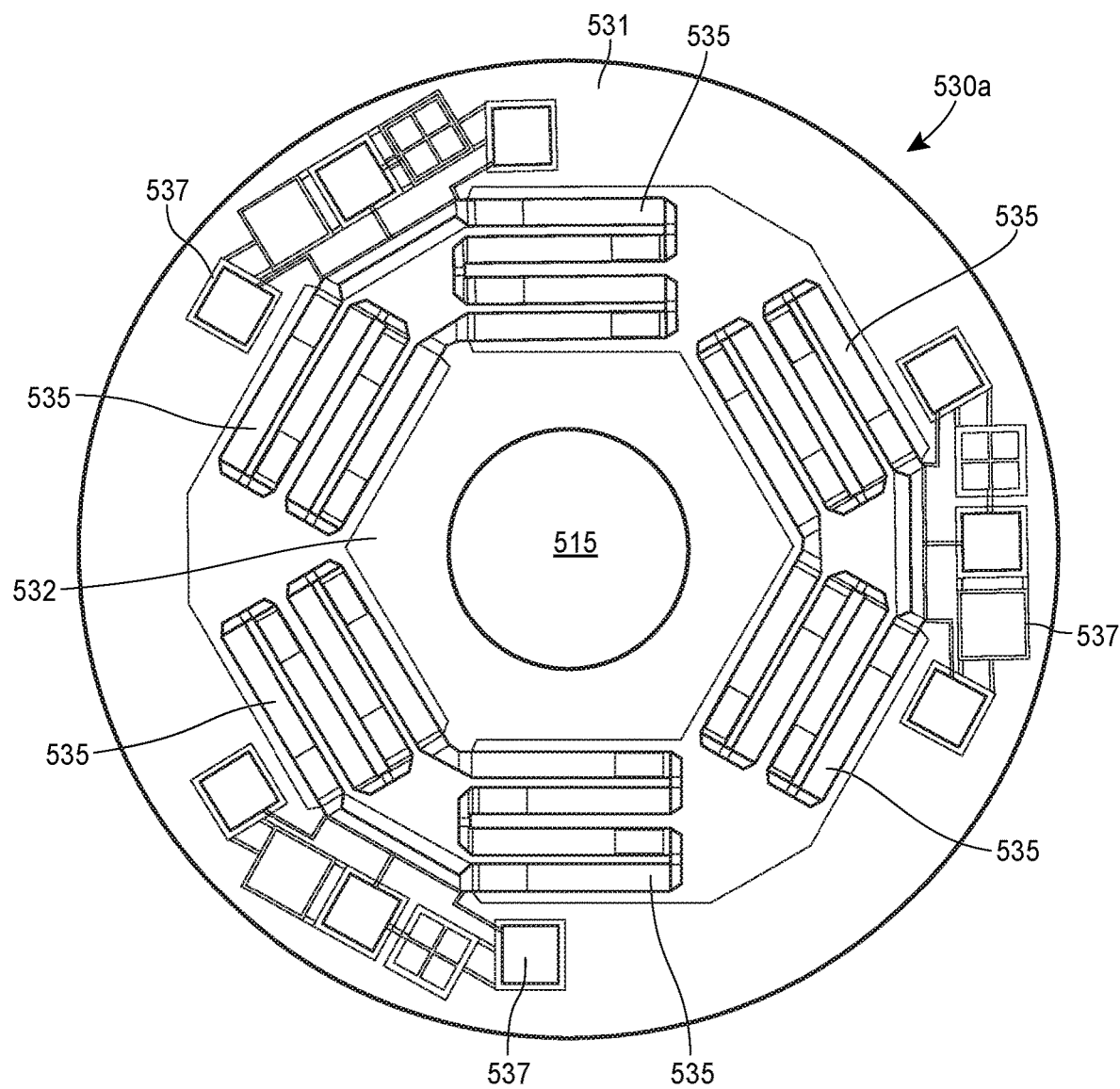
FIGS. 6 and 7 are top plan views of the example axial scanning actuator of FIG. 5 in accordance with various embodiments.
Figure 7:
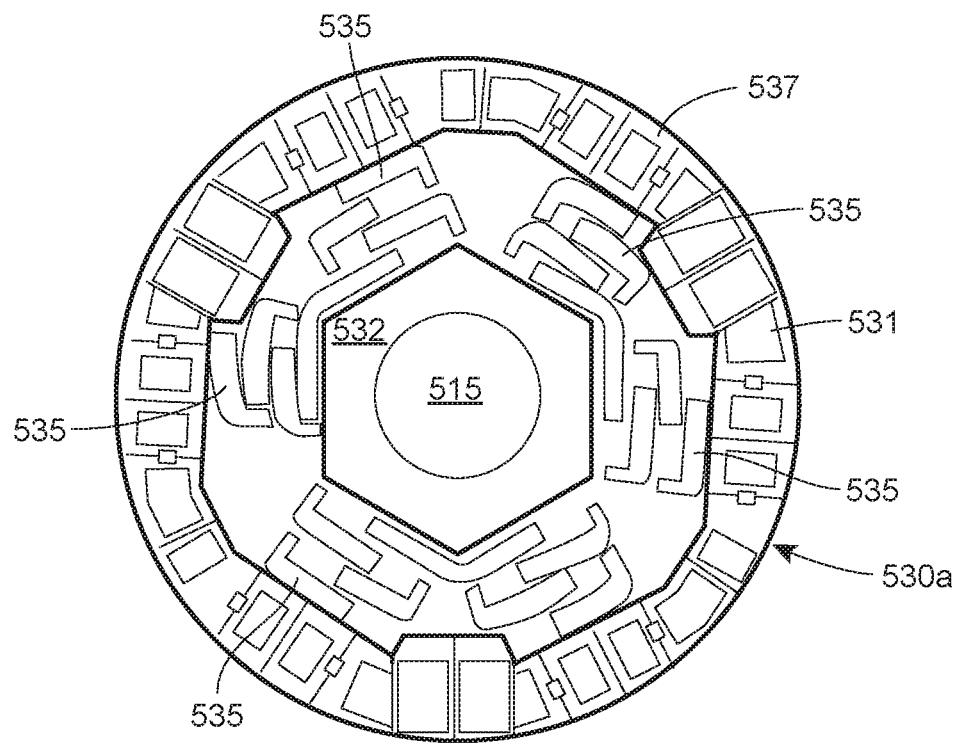
Figure 8:
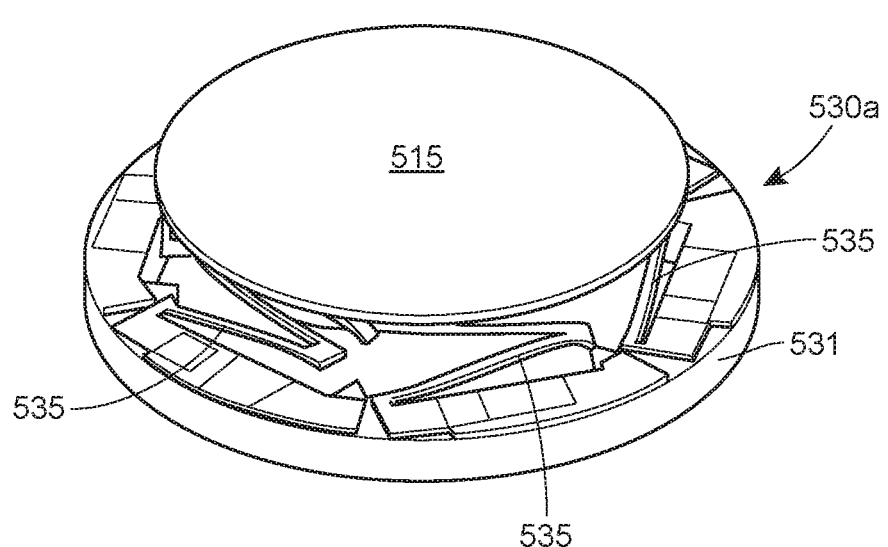
FIG. 8 is a perspective view of the example axial scanning actuator of FIGS. 5-7 whereby actuator legs are extended to create displacement in accordance with various embodiments.
Figure 9:
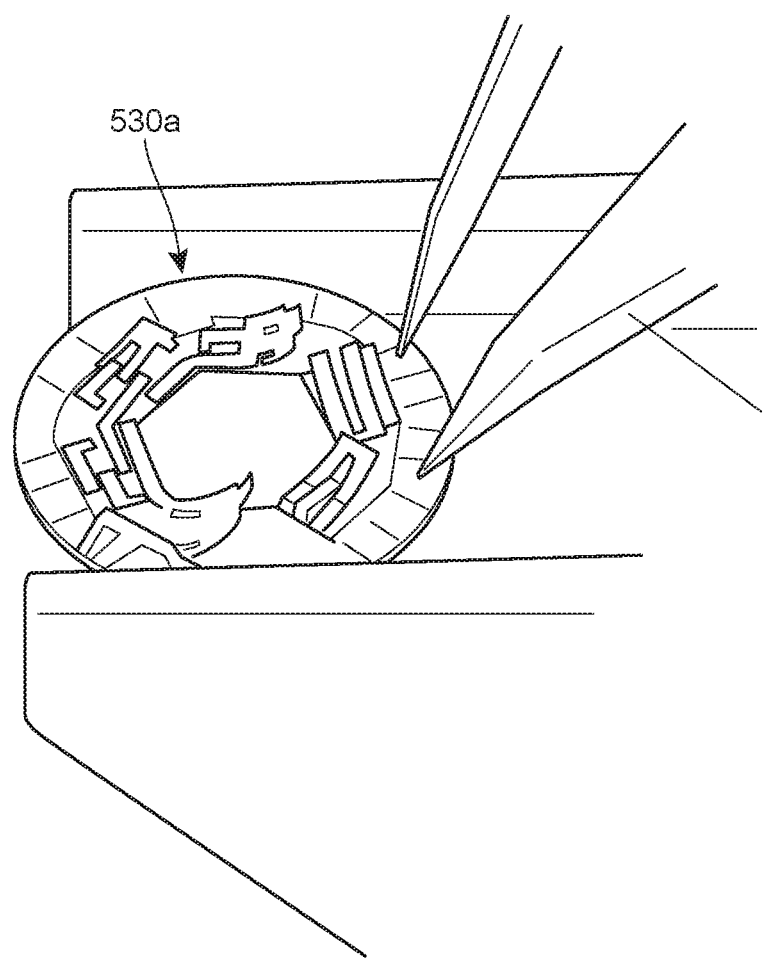
FIG. 9 is a perspective view of the example axial scanning actuator of FIGS. 5-8 in a completed configuration in accordance with various embodiments.

FIG. 2 provides a more detailed illustration of the probe 100, which uses a remote axial scanning architecture in which both axial and lateral scanning are performed prior to the distal optics, with axial scanner translation mirrored at the objective. Such an architecture can support small diameter distal optics with a compact, handheld form factor. In this approach, lateral scanning is performed by an electrostatic rotational scanning mirror.

Each of the axial scanning unit 130 and the lateral scanning unit 140 may employ an electrostatic actuation design and one that uses parametric resonance for operation. In some examples described herein, actuation via the axial scanning unit 130 is achieved through a piezoelectric (PZT) actuator that is assembled or formed onto to a mounting fixture, with the actuator manually positioned to eliminate any static off-axis tilt of the scanning mirror. Each actuator includes a mirror or mirror surface that is placed before the axial scan or lateral scan objective.

The previously-mentioned laser and light collection electronics can include a Ti-Sapphire laser 104 with a tunable spectral range of approximately 690-1040 nm. This laser 104 delivers excitation 105 with approximately 100 fs pulse width at 80 MHz. The pulse duration may be minimized using a dispersion pre-compensation unit located inside the laser housing. A half wave plate 106 is used with a linear polarizer 107 to adjust laser power. The beam is initially p-polarized after passing through a polarizing beam splitter (PBS) 108. After passing through a quarter wave plate (QWP) 109, reflecting off of the lateral scanning mirror 110 (M1) of the lateral scanning unit 140, and passing back through the QWP 109, the beam becomes s-polarized.

After reflecting off the PBS 108 at 90°, the excitation beam is expanded by a first lens 111 ($L_1$) with a focal length of approximately 35 mm and a second lens 112 ($L_2$) with a focal length of approximately 100 mm to fill the back aperture of the first objective lens 113. A second PBS 114 reflects the beam through a QWP 116 onto the axial scanning mirror 115 (M2). The wavefront then passes back through the QWP 116 and PBS 114, and is then expanded by a pair of telescope lenses 117 ($L_3$) and 118 ($L_4$), both with focal lengths of 75 mm. The beam then reflects off of a dichroic mirror 119 (DM) at 90°, and fills the back aperture of a second objective lens 120 (Obj$_2$), which in this example is a water immersion lens. As the surface of the axial scanning mirror 115 of the axial MEMS scanning unit 130 moves in the axial direction. Translation of M2 115 results in axial displacement of the focus below the tissue surface of the specimen with a magnification of less than an approximate 2:1 ratio.

As illustrated in FIG. 2, fluorescence 122 generated from the sample 103 passes through DM 119, reflects off a planar mirror 123 (M$_3$), and is focused by a first lens 124 (L5) having a focal length of 60 mm and a second lens 125 (L6) having a focal length of 35 mm, and through a band pass filter 126 (BPF; approximately 80% transmission between approximately 380-580 nm), and onto a photomultiplier tube detector (PMT) 127. The photomultiplier tube signal is amplified by a high-speed current amplifier (not shown). High-speed data acquisition boards digitize the fluorescence signal from the photomultiplier and generate control signals to drive both the axial scanning unit 130 and the lateral scanning unit 140. In some examples, different, optimized drive signals may be sent to individual mirrors and/or actuating legs. A first board is used for signal acquisition, and a second board is used to control waveform generation a personal computer using custom software can be used to control and synchronize the data acquisition boards. A channel from the signal acquisition board may be used to digitize a voltage signal having a desired sample rate (e.g., 10 M samples per second). Any number of channels (for example, three) can be used in the waveform generation board to generate waveforms having a desired sample speed (e.g., 1 M samples per second) to control the three scanning axes. In order to map a one dimensional digitized signal to a 2D image, it is important to ensure signal acquisition and waveform generation are precisely synchronized. A real-time system integration (RTSI) cable may be used between the two boards such that they can share an identical timing source and start trigger to remain synchronized. Customized software is written in Labview to calculate the control waveform and send data to the waveform generation board while reading data from the signal acquisition board. The software can also choose to actuate either only the lateral scanner for the horizontal imaging mode or both the lateral and axial scanners for the vertical imaging mode. By actuating different axes of the two scanning units 140, 130, the scan direction can be changed between the horizontal (XY) and vertical (XZ) planes in the sample.

Distinct electrostatic MEMS scanners are provided for lateral and axial scanning based on the principle of parametric resonance. Large mechanical actuation can be achieved by driving the structure at $2\omega_0/n$, where $\omega_0$ is the natural frequency of the scanner and n is an integer $\geq 1$. FIG. 3A illustrates the mirror 110 that is formed as part of a lateral actuator system 140a of the lateral scanning unit 140. While the mirror 110 may take different shapes, in the illustrated example, the mirror 110 is a circular mirror. In the illustrated example, the diameter is 1.8 mm and the mirror 110 is able to accommodate an excitation beam having a width of 1.27 mm width at normal incidence (as opposed to 45°). The front-side of lateral actuator system 140a was coated with aluminum to achieve reflectivity greater than approximately 85% between approximately 200-900 nm wavelengths to reflect a range of wavelengths for multiphoton excitation.

In the illustrated example, the lateral actuator system 140a includes two actuating axes, about which, the mirror 110 may be independently rotated. An X-axis is defined as shown, aligned with inner leg or spring members of an inner mirror actuator. A Y-axis is defined as aligned with an outer leg of an outer mirror actuator. Each leg is part of an inner and outer comb filter drive, respectively. The comb filter drivers provide electrostatic actuation, such that the mirror 110 rotates around inner (X-axis) and outer (Y-axis) axes, respectively, when driven by drive signals. Each of the inner and outer comb filter drives may be operated at a resonant frequency, e.g., a resonant frequency chosen to be between approximately 1 kHz and approximately 4 kHz, respectively. Furthermore, the system 140a may be driven, with select resonant frequency drive signals to each comb drive, such that the mirror 110 undergoes a sinusoidal scanning pattern. In an example, the system 140a is driven by resonant frequencies to image at ≥5 frame/sec using a Lissajous scanning pattern, and scanning at 400×400 pixels per frame.

Both the inner and outer axes of the lateral actuator system 140a can be actuated to image in the horizontal (XY) plane. The resonant frequencies of these axes were designed to be approximately 1 kHz or 4 kHz, respectively. Further, by combining actuation of the inner axis of the lateral scanner with the out-of-plane motion of an axial scanner, images can be produced in the vertical (XZ) plane. When scanning an object, a dense Lissajous scan pattern is formed that repeats itself at 5 frames per second to generate either horizontal or vertical images with dimensions of 400×400 pixels or 400×320 pixels at 100% coverage. The MEMS scanners are driven via customized software developed in LabView that also reconstructs the image by remapping the time series signal to a 2D image using calibrated motion profiles from the scanner to generate a lookup table. In other words, by knowing where the laser was directed at a particular time, the intensity of the returning laser light can be mapped to form a 2D image. The relationship between the displacement of the axial actuator system 130 and the point of focus in the specimen 103 is quantified by mounting the axial actuator on a motorized stage to accurately control position. Advantageously, vertical sections may be collected at approximately 5 frames per second compared to conventional imaging devices which can require several minutes to acquire a stack of horizontal sections and reconstruct corresponding vertical sections.

The lateral actuator system 140a may be formed on a chip having a size of 3×3 mm$^2$. The mirror 110 is mounted on a gimbal frame 141 to minimize cross-talk between axes, i.e., between the inner and outer axes drives. The lateral actuator system 140a operates at an increased resonant frequency in order to scan at higher frame rates. Orthogonal sets of electrostatic comb-drive actuators 145a, 145b are coupled to the inner and outer torsional legs or springs 144a, 144b and determine the resonant frequencies of the scanner, based on their shape and configuration. FIGS. 3B & 3C illustrate measured angular deflection of the lateral MEMS scanner 140 in either axis as frequency response of the scanner to a sine-wave input at 60 $V_{pp}$ for the lateral (i.e., horizontal) X-axis and Y-axis, respectively. Large scan angles can be achieved with either a downsweep or an upsweep, but greater deflection angles were achieved with a downsweep. For both the X-axis and the Y-axis, in the illustrated example, the lateral scanner 140 can achieve >5° mechanical scan angle at 60 $V_{pp}$ with a drive frequency close to 8.2 kHz and 2 kHz. Drive frequencies of 8570 Hz and 2100 Hz were used to produce actual tilt frequencies of 4285 Hz and 1050 Hz in the X and Y axes, respectively. The result was a dense Lissajous scan pattern that repeated itself at 5 Hz to encompass images with dimensions of 400×400 pixels with 100% coverage for a FOV of 250×250 µm$^2$.

In some examples, a control system can be configured to achieve Lissajous scanning. Due to increased actuator motion uniformity, Lissajous scanning is used if the axial mirror scanning frequency is too close to the lateral mirror scanning frequency. By tailoring the axial actuator designs to operate at specific frequencies, a fast Lissajous frame rate is obtained.

Details of the axial scanning unit 130, specifically the axial actuator system 130a, are now discussed in reference to FIGS. 4A-9. A one-dimensional resonant MEMS scanner has an out of plane (axial) translation of more than approximately 400 µm at 50V along the optical axis to create images in the plane perpendicular to the tissue surface. This displacement will provide more than approximately 200 µm axial displacements below the specimen, which is sufficient to image through the epithelial layer. A circular axial scan mirror (or reflector) 115 with a diameter of 2 mm is attached to a mirror platform 132 and is attached on two U-shaped levers 133 via serpentine springs 134 located at each corner. Four columns of electrostatic comb drive actuators (e.g., comb-drives 135) are disposed on each side of the mirror 115 to provide large driving force on each lever, which results in rotational motion of the lever 133 about the Y-axis. Rotating both levers 133 in phase results in out-of-plane displacement of the circular mirror 115. However, the mirror 115 rotates about the Y-axis when the two levers 133 are out of phase. Therefore, in-phase drive signals are provided to the two different comb drives 135, when axial scanning (i.e., along the Z-axis) is desired from an otherwise stable, flat mirror. Out-of-phase drive signals or some combination of in-phase and out-of-phase drive signals would be used when a combined axial scanning and rotational scanning are desired. The serpentine springs 134 determine the resonant frequency for each comb drive 135 and they determine the resonant frequency for each scanning mode, i.e., axial (or vertical) scanning mode and rotational scanning mode. The springs 134 are designed to increase the spacing in frequency between the vertical and rotational modes to avoid crosstalk during actuation. In an example, the resonant frequency was approximately 500 Hz for vertical motion.

In order to provide a clear image, the axial scan mirror 115 is positioned at the same axial distance as the working distance at the objective lens 120, and remains aligned such that the vertical axis of the mirror 115 is along the same axis as the lens and laser path. Such an alignment relies upon horizontal alignment of the mirror 115 such that the laser is centered thereon.

For the axial scanning mirror 115, the frequency response is characterized by measuring the out-of-plane displacement using a laser displacement sensor. The scanner performance was measured by sweeping the drive frequency applied to the actuator at various voltages and duty cycles using either an upsweep (low-to-high) or downsweep (high-to-low) in frequency.

Like the lateral scanning unit 140, the axial scanning unit 130 may be formed on a chip sized at 3.7×3.2 mm$^2$; and the mirror 115 is approximately 2 mm in diameter. As illustrated in FIG. 4B, the frequency response of the axial scanning unit 130 is shown by sweeping the drive frequency between 870 Hz and 1000 Hz using a 60 V$_{pp}$ square wave with 30% duty cycle. Unlike the lateral scanning unit 140, the axial scanning unit 130 has a larger displacement during an upsweep. For imaging, the scanner is actuated with a drive frequency at 930 Hz, resulting in an axial displacement of more than 400 µm at a drive frequency of 930 Hz which results in actuation at 465 Hz from the parametric resonance effect. Note, the resonant frequency of the axial scanning unit 130 is over a different frequency range than the lateral scanning unit 140, which allows for better individualized control over each scanning modality.

In some examples, substantially large differences in mirror deflection amplitudes for upsweep versus downsweep may be observed that are caused by a softening effect in the springs. At further distances from the static mirror position, electrostatic forces are reduced, which can result in a dynamic bifurcation with two stable modes. One such node occurs at the origin, and a second node occurs at the stable limit cycle that produces large deflections. The largest deflections may be observed when approached from higher frequencies (e.g., during downsweeps) due to a gradual increase in oscillation amplitude from a softening resonant peak being tilted in this direction. When approached from lower frequencies (e.g., during upsweeps), the origin remains at the stable bifurcation branch until the point where upsweep and downsweep responses converge. In some examples, the opposite effect may occur for the axial scanning unit 130.

As illustrated in FIGS. 4C & 4D, respectively, the axial MEMS scanning unit 130 is provided under a laser displacement sensor (not shown) that generates the illustrated laser beam spot 139, before and after a drive signal is applied.

As illustrated in FIGS. 4E-4G, the wavefront of the excitation beam changes as the mirror surface of the axial mirror 115 moves in either direction away from the neutral position (ZM2=0 µm) illustrated in FIG. 4E. When the mirror 115 is 200 µm away from the first objective lens 113 (ZM2=−200 µm), the wavefront converges onto the second objective lens 120, and the focal plane moves approximately 100 µm toward the tissue surface as illustrated in FIG. 4F. Similarly, when the mirror 115 moves closer to the first objective lens 113 (ZM2=200 µm), the wavefront diverges, and the focal plane moves axially with greater depth into the tissue as illustrated in FIG. 4G.

The excitation beam may become miss-aligned if the mirror surface of the axial scanning mirror 115 tilts during translation. Accordingly, a position sensing detector (PSD) is used to measure the tilt angles about the X and Y axes during axial displacement over the range of drive frequencies. A maximum tilt angle of <0.004° was measured in the X axis (see FIG. 4H), and a maximum tilt angle of <0.19° was measured in the Y axis (see FIG. 4I), when the mirror is driven at 930 Hz. A rotational mode for this scanner was observed at less than approximately 1200 Hz, which is out of the operating range of the actuator. These results illustrate large axial scan displacements in the Z-axis can be achieved with very small tilt angles in either the X or Y axes. Also, by properly designing the spring parameters and locations, we can separate the frequency range between axial scanning and rotational (i.e., tilting) scan modes for the axial scanning unit 130. Such a high performance axial (i.e., vertical) scanner can enable axial beam scanning using a remote scan setup with less than 10% power variation.

As illustrated in FIG. 4J, a linear relationship was observed between the location of the focal plane and that of the axial MEMS mirror 115. The axial resolution, defined by the FWHM, varies from 4.5 to 7 µm over the scan range of mirror 114 as illustrated in FIG. 4K. With the mirror 115 in the neutral position, a lateral FOV of 270×270 µm$^2$ was measured. Upon translating mirror 115, the lateral magnification decreases from approximately 1.2 to 0.9 as the focal plane moves from −100 µm to 100 µm from the neutral position, and the lateral FOV decreases from 320 µm to 240 µm. This difference results from a slight mismatch in the optical parameters between the first and second objective lenses 113, 120, which are air and water immersion lenses, respectively.

An example arrangement of an axial actuator system 530*a* using thin-film piezoelectric actuation is provided in FIGS. 5-9 and includes a silicon frame 531, a mirror platform 532 that a mirror 515 is disposed on, a plurality of actuator legs 535 which provide a driving force, and a plurality of bond pads 537 for electrical coupling. It is understood that the axial actuator system 530*a* may include any number of additional components for proper operation. In this example arrangement, the components, and in particular the legs 535, are distributed in a circular array about the mirror platform 532. In some examples, each of the legs 535 can be distributed equidistant from the midpoint of the mirror platform 532, while in other examples, any number of the legs 535 can be distributed at different lengths from the mirror platform 532. The legs 535 are distributed in the circular array to enhance stability of the mirror platform when the legs 535 are actuated, thus reducing the occurrence of artifacts during imaging. In other words, the legs 535 can be paired such that pairs of legs 535 are on opposing sides of the mirror and extend in a radial direction approximately 180 degrees apart. However, in some examples, three evenly spaced sets of legs 535 can be disposed about the mirror platform 532 at approximately 60 degrees away from each other. Other examples are possible. The legs can be attached to the silicon frame 531 at an outer support structure and can be attached to the mirror platform 532. The piezoelectric and electrode layers extend over the top of the silicon frame 531. Typically, the area where the piezoelectric layer overlaps is reinforced with a layer of gold or other metal. In some examples, a thick polymer coating is used as reinforcement.

In some of these examples, the legs 535 are configured to apply a symmetric piezoelectric force to the mirror platform 532. In other words, the strength of the forces on the mirror platform 132 may be evenly distributed among the legs 535. For example, if a pair of legs 535 are disposed equidistant from the mirror platform 532, each individual leg 535 can be adapted to apply an equal force to the mirror platform 532. Conversely, if a pair of legs 535 are not equidistant from the mirror platform 532, one of the two legs 535 can apply a greater force than the other leg 535 in order to apply a combined symmetric piezoelectric force on the mirror platform 532. It is understood that any number of actuator legs 535 may cooperate to apply the symmetric piezoelectric force.

Each of the legs 535 may include any number of individual sections that cooperate to generate axial movement of the mirror platform 532. The individual sections may be configured in a switch-back (or serpentine) pattern in a horizontal plane whereby torsional segments connected to each other at adjacent ends create extension about the connection points.

In the illustrated example, a number of aluminum pads are disposed on the top and the bottom electrodes of the actuator legs 535. Due to the small size of these components, it may be difficult to create strong electrical connections between the actuator legs and the bond pads 537. A parylene bridge and other material layers are deposited on the actuator legs 135 to create electrical jumpers or connections from the top and bottom electrodes of the PZT film to the bond pads 537.

Additionally, any number of the actuator legs 535 may have any number of piezoresistive sensors coupled thereto to provide an accurate measurement of vertical position. As previously stated, this optical arrangement relies on uniform vertical motion of the axial scanner. The sensors provide a feedback mechanism for adjusting voltage at individual legs to balance the vertical motion and provide a more uniform movement. In some examples, the sensors can provide feedback to control the actuators using a closed-loop control system.

As illustrated in FIGS. 10 and 11A-G, the actuators are fabricated with a silicon-on-insulator wafer with 30 μm device layer. First, narrow trenches are etched by deep reactive-ion etching (DRIE) to the buried oxide layer, and refilled by tetraethyl orthosilicate (TEOS) chemical vapor deposition (CVD) silicon dioxide (FIG. 11A). The top surface of the wafer is chemically-mechanically polished and coated with an additional high temperature low pressure chemical vapor deposited (LPCVD) silicon dioxide that provides a uniform base layer for PZT deposition. The isolated structures in the device layer produced by this step become precisely defined rigid silicon elements of the completed platform, such as the frame and mirror platform.

Bottom electrode (Ti/Pt, 200 nm), piezoelectric (PNZT seed/chemical solution PZT, 1.2 μm) and top electrode (Pt, 120 nm) are next deposited on the prepared wafer and are sequentially patterned by reactive-ion etching (RIE). As seen in FIG. 11B, structural aluminum layer (1 μm) is then patterned by a lift-off process to the top surface of select regions of the electrodes to improve bond-pad strength and adjust the neutral axis of bend-down portions of cantilever beams. As previously mentioned and as illustrated in FIGS. 10 and 11C, to improve reliability of electrical interconnects, a parylene-C film (560 nm), silicon dioxide (230 nm) layer, and additional aluminum layer (1 μm) are deposited to create electrical jumpers from the top and bottom electrodes of the PZT film to bond pads patterned directly on the silicon dioxide wafer surface has significantly better reliability for wire bonding necessary in the confined space of endomicroscopy instruments.

A series of deep trench etching steps were used to release the actuator legs 135 from the silicon wafer. First, as seen in FIG. 11D, silicon DRIE and silicon dioxide RIE steps were performed to etch through the buried oxide between actuation legs. Next, two-level backside DRIE is performed, with initial etching beneath individual actuator legs (FIG. 11E), and then full backside area etching beneath all moving parts (FIG. 11F). By etching the silicon dioxide layer exposed initially by the deeper portion of the backside etch before completing the backside DRIE process, free-standing thin-film PZT beam elements could be released, while retaining a solid silicon platform as a mirror platform or as the mirror itself (FIG. 11G). During this last release step, non-uniform etching of silicon or the formation of micro-columns can be handled with $SF_6$ or $XeF_2$ etching thanks to the silicon-dioxide-filled trenches formed in the earlier step (FIG. 11A). With optimized etching parameters and layer thicknesses, the formation of the protective silicon dioxide trenches in the device layer (FIG. 11A) can be omitted.

Two photon excited fluorescence intensity has a nonlinear relationship with photon flux at the focal point, thus laser intensity must be stable when the axial scanning unit 130 is out-of-plane. In fabrication of the actuator system 130*a*, the DRIE and other processes may cause asymmetry in the structure of the legs. Therefore, large out-of-plane motions may cause the mirror surface to incur small tilt angles and can accordingly defocus the beam. To determine how the tilt angle affects imaging, ray-trace simulations were performed. A model with paraxial lenses was developed that has the same focal lengths as lenses 113 and 120. A point spread function is used with the axial scanning unit 130 at different axial locations and with different tilt angles when the mirror is scanning. The peak intensity of the axial point spread function can be used as a metric to evaluate change in laser power at the focal spot.

Using this model, it is possible to determine required axial displacement and mirror size for the axial MEMS scanner 130. This information can be used to design the parameters of the MEMS scanner in order to achieve a field-of-view of 250×250 µm² in either the horizontal or vertical plane with a peak intensity variation less than 10% during axial scanning.

To demonstrate the performance of the axial MEMS scanner 130, autofluorescent pollens having a diameter of approximately 30-40 µm were imaged in both XY and XZ planes. A 3D stack of images collected in the horizontal (XY) plane was taken by moving the sample 50 µm in the axial direction with 1 µm step size. The vertical projection (XZ) was then reconstructed and compared with the image collected in the vertical plane (XZ) with the axial scanner.

From the simulation result, the displacements of the axial scanning unit 130 and the focal spot has a magnification around 1:1. Results for the change in point spread function for either a 100 µm upward displacement (FIGS. 12A-C) or 100 µm downward displacement (FIGS. 12D-F) of the axial scanner in the Z-axis, with tilt angles of 0°, 0.8°, and 1.6°, are shown. From the results of the simulation, tilt angles as small as 1.6° can reduce the peak intensity by more than 20%.

Turning to FIGS. 13A-C, FIG. 13A is an XY image of the pollens under horizontal scanning mode, with a field of view of 100×100 µm². Horizontal images were collected while moving the specimen axially in 50 µm increments. A vertical image was extracted from the subsequent 3D reconstruction as illustrated in FIG. 13B. By comparison, we collected an image in the vertical plane directly by translating the mirror 115 in FIG. 13C both type of XZ images have a field of view of 100×50 µm². No apparent resolution or intensity change was observed between these two types of vertical images. In other words, the same intensity of returning light as a function of imaging depth was seen regardless of whether XY or XZ scanning was performed.

FIG. 14A is a representative image of the specimen obtained in the horizontal (XY) plane over a FOV of 270×270 µm² showing a distinct crypt structure. Hexagonally packed, circularly-shaped crypts (as indicated by the arrow) with uniform dimensions surrounding a central lumen (l) can be distinguished. Mucin-filled goblet cells (g) can be seen within cytoplasm (c) that produces uniform fluorescence. Individual inflammatory cells (arrowhead) can be identified in the lamina propria (lp). FIG. 14B is an XZ images at the same location, with a field of view of 270×200 µm². The lumen (l) is now oriented vertically, and goblet (g) cells are seen distributed in the apical to basilar direction.

FIGS. 15-16D illustrate an alternative design for an axial actuator system 630a. The alternative design can accommodate additional square actuators onto a silicon wafer. A central mirror or mirror platform 632 is supported by four serpentine piezoelectric bending beams, legs, or actuators 635, with piezoelectric stack materials varied to produce selective bend-up or bend-down motion in successive segments of the beams 635. This results in well-defined vertical translation of the mirror surface 632, further enforced by symmetry of the structure in ideal conditions.

The axial actuator system 630a has overall dimensions of approximately 3 mm×3 mm×0.5 mm, for eventual integration into 5 mm diameter or smaller endomicroscopy instrument, and an actuator 635 design including four 1.2 mm long individual beams to produce about 400 µm of vertical (i.e., out of plane) displacement along the optical axis to create images in a plane perpendicular to the tissue surface with a natural frequency of about 100 Hz. The actuators 635 are operated near-resonance, with Lissajous scanning used to extract images from the combined motion of the vertical piezoelectric actuators and an in-plane electrostatic scanning mirror. Use of resonant operation enables large scanning range at low voltages, as well as dynamic balancing of the mirror for uniform vertical motion even with a just a single input to the four actuation legs.

The foregoing description demonstrates a novel multiphoton microscope that uses a remote scan configuration and MEMS scanners to provide real time switchable XY/XZ imaging. The axial MEMS scanner works under resonant mode with mechanical resonant frequency of around 440 Hz, resulting in a line scan rate of 880 Hz for a range of 200 µm. This high speed axial scanning technique could be used to study fast biological processes, such as action potentials between neurons, in live animals. Although ultra-fast pulses are focused onto the axial MEMS, no signs of damage of the mirror surface were observed after an hour of exposure under 50 mW laser power. The damage threshold could be further improved by changing the mirror coating from aluminum to gold. The lateral MEMS scanner also operates under resonant mode with resonant frequencies of around 4 kHz and 1 kHz for the inner and outer axes. Lissajous scanning was used for both horizontal or vertical plane imaging, with FOVs of 250 µm×250 µm and 250 µm×200 µm respectively and a frame rate of 5 Hz. These MEMS scanners are extremely compact, with footprints about 3 mm×3 mm, while maintaining good mechanical properties. They are also highly reliable, low cost and can be easily mass produced. These MEMS scanners can be good alternatives to the bulky actuators used in conventional microscopes. By using this scanning strategy, it is possible to develop an ultra-compact intravital microscope, or even a miniature device, with real time horizontal and vertical sectioning capabilities. Additionally, in some systems, axial scanning can be completed using electrothermal, electromagnetic, and/or other microactuators in arrangements having similar geometries to the axial scanning actuators described herein, or using electrostatic actuators with offset electrodes to achieve low-frequency (DC) scanning.

In large displacement vertical stages that rely on bending beam architectures, central stage motion can be very sensitive to asymmetries in individual legs, which can result from local variations in residual stress, photolithography misalignment, or other processing non-idealities. One way to deal with non-uniform central stage motion is to calibrate and compensate for asymmetries by applying distinct voltages to two or more legs. Uniform vertical motion can be achieved by identifying frequencies in which contributions from multiple vibration modes produce nearly pure vertical translation, allowing balancing to be performed with just a voltage input to the stage.

Figure 17:
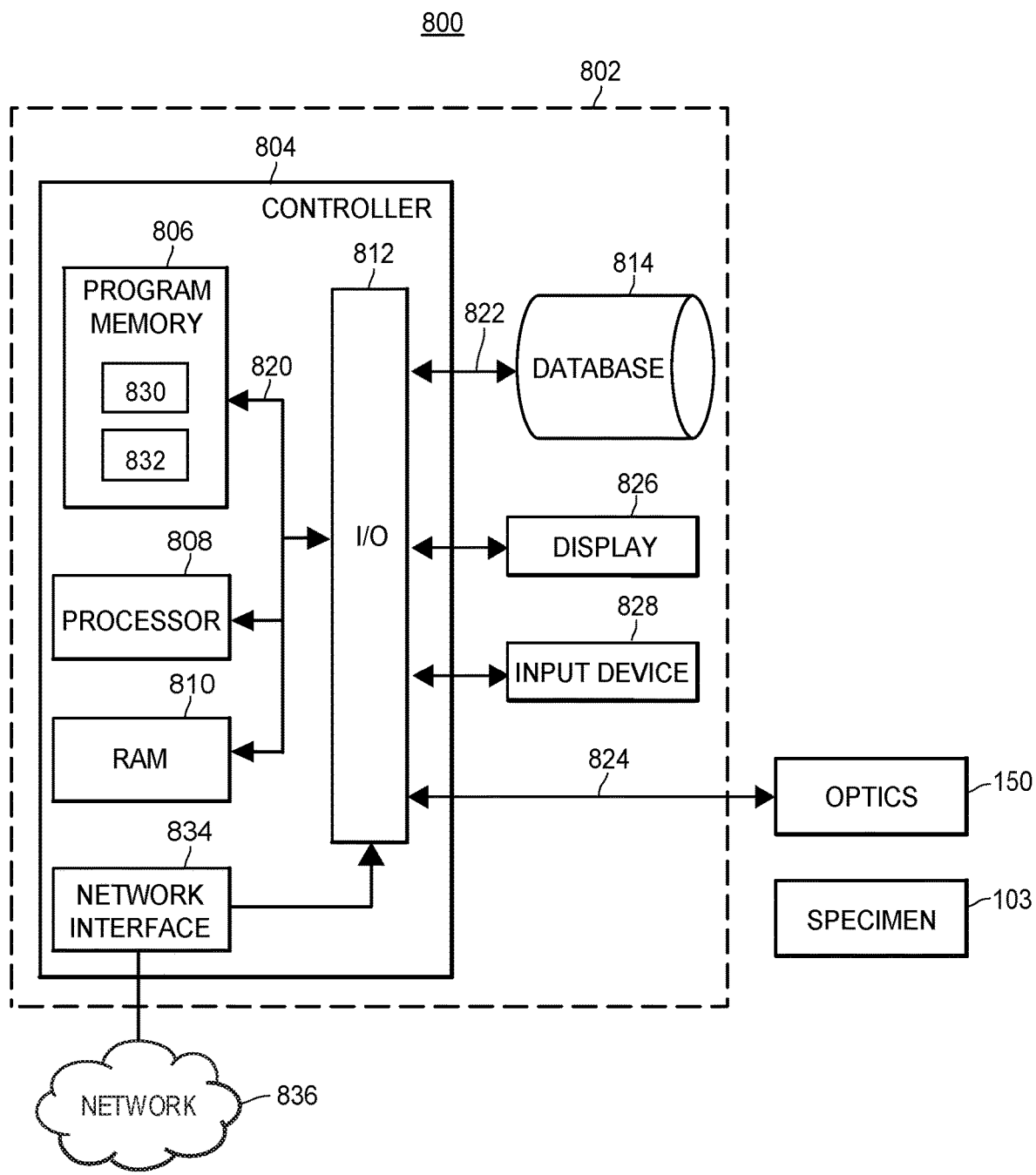
FIG. 17 depicts an example block diagram illustrating various components used in implementing an exemplary embodiment of the thin-film piezoelectric multi-photon endomicroscope in accordance with various embodiments.

FIG. 17 is an example block diagram 800 illustrating the various components used in implementing an example embodiment of the thin-film piezoelectric multi-photon endomicroscope 802 discussed herein. The optics 150 previously discussed herein may be positioned adjacent or operatively coupled to a specimen 103 in accordance with executing the functions of the disclosed embodiments. The device 802 may have a controller 804 operatively connected to the database 814 via a link 822 connected to an input/output (I/O) circuit 812. It should be noted that, while not shown, additional databases may be linked to the controller 804 in a known manner. The controller 804 includes a program memory 806, the processor 808 (may be called a microcontroller or a microprocessor), a random-access memory (RAM) 810, and the input/output (I/O) circuit 812, all of which are interconnected via an address/data bus 820. It should be appreciated that although only one microprocessor 808 is shown, the controller 804 may include multiple microprocessors 808. Similarly, the memory of the controller 804 may include multiple RAMs 810 and multiple program memories 806. Although the I/O circuit 812 is shown as a single block, it should be appreciated that the I/O circuit 812 may include a number of different types of I/O circuits. The RAM(s) 810 and the program memories 806 may be implemented as semiconductor memories, magnetically readable memories, and/or optically readable memories, for example. A link 824 may operatively connect the controller 804 to the optics 150 through the I/O circuit 812.

The program memory 806 and/or the RAM 810 may store various applications (i.e., machine readable instructions) for execution by the microprocessor 808. For example, an operating system 830 may generally control the operation of the endomicroscope 802 and provide a user interface to the testing apparatus to implement the processes described herein. The program memory 806 and/or the RAM 810 may also store a variety of subroutines 832 for accessing specific functions of the endomicroscope 802. By way of example, and without limitation, the subroutines 832 may include, among other things: a subroutine for controlling operation of the optical device 150, or other endoscopic device, as described herein; a subroutine for capturing images with the optics 150 as described herein; and other subroutines, for example, implementing software keyboard functionality, interfacing with other hardware in the endomicroscope 802, etc. The program memory 806 and/or the RAM 810 may further store data related to the configuration and/or operation of the endomicroscope 802, and/or related to the operation of one or more subroutines. For example, the data may be data gathered by the optics 150, data determined and/or calculated by the processor 808, etc. In addition to the controller 804, the endomicroscope 802 may include other hardware resources. The endomicroscope 802 may also be coupled to various types of input/output hardware such as a visual display 826 and input device(s) 828 (e.g., keypad, keyboard, etc.) to fine tune actuation of the axial and lateral scanners. In an embodiment, the display 826 is touch-sensitive, and may cooperate with a software keyboard routine as one of the software routines 832 to accept user input.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A multi-photon optical probe comprising:
    a probe housing having a proximal end and a distal end positioned at a sample, the probe housing adapted to produce an output laser energy;
    a lateral scanning stage coupled to a lateral mirror assembly and at least partially being disposed in the probe housing, the lateral scanning stage adapted to scan the output laser energy over a planar scan area of the sample by moving the lateral mirror assembly; and
    an axial scanning stage coupled to an axial mirror assembly and at least partially being disposed in the probe housing, the axial scanning stage adapted to scan the output laser energy over a depth range of the sample, wherein the depth range and the planar scan area form a 3-dimensional volume;
    wherein the axial scanning stage comprises a plurality of actuating legs positioned in a horizontal plane axially about the axial mirror assembly, and
    wherein the lateral scanning stage and the axial scanning stage are independent scanning stages positioned to provide single axis multi-photon probing.

2. The multi-photon optical probe of claim 1, wherein the plurality of actuating legs are positioned symmetrically about the axial mirror assembly.

3. The multi-photon optical probe of claim 1, wherein the axial scanning stage comprises at least one sensor adapted to sense a displacement of the at least one of the plurality of actuating legs.

4. The multi-photon optical probe of claim 3, wherein the at least one sensor comprises a piezoresistive sensor disposed on at least one actuating leg.

5. The multi-photon optical probe of claim 1, further comprising a plurality of electrical connectors positioned axially about the axial mirror assembly.

6. The multi-photon optical probe of claim 5, wherein each of the plurality of electrical connectors comprises an electrical jumper extending from a top and a bottom electrode to a bond pad patterned on the axial scanning stage.

7. The multi-photon optical probe of claim 6, wherein the electrical jumper comprises a parylene film, a silicon dioxide layer, and a metallic layer.

8. The multi-photon optical probe of claim 1, further comprising distal optics adapted to scan the sample.

9. The multi-photon optical probe of claim 8, wherein the distal optics have a diameter of less than 3.4 mm.

10. The multi-photon optical probe of claim 1, further comprising laser and light collection electronics at least partially disposed in the probe housing, the laser and light collection electronics comprising a half wave plate, a linear polarizer, and at least one lens.

11. The multi-photon optical probe of claim 8, wherein the lateral scanning stage, the axial scanning stage, and the distal optics are coupled via fiber optical connections.

12. An axial scanning stage for a multi-photon optical probe, the axial scanning stage comprising:
    a frame;
    a mirror platform coupled to the frame, the mirror platform adapted to support a mirror element;
    a plurality of actuator legs coupled to the frame and the mirror platform, the plurality of actuator legs adapted to raise the mirror platform along a vertical axis; and
    a plurality of electrical connectors positioned about the mirror platform;
    wherein the plurality of actuator legs and the plurality of electrical connectors are positioned axially about the mirror platform.

13. The axial scanning stage of claim 12, wherein the plurality of actuating legs and the plurality of electrical connectors are positioned symmetrically about the axial mirror assembly.

14. The axial scanning stage of claim 12, further comprising at least one sensor adapted to sense a displacement of the at least one of the plurality of actuating legs.

15. The axial scanning stage of claim 14, wherein the at least one sensor comprises a piezoresistive sensor disposed on at least one actuating leg.

16. The axial scanning stage of claim 12, wherein each of the plurality of electrical connectors comprises an electrical jumper extending from a top and a bottom electrode to a bond pad patterned on the axial scanning stage.

17. The axial scanning stage of claim 16, wherein the electrical jumper comprises a parylene film, a silicon dioxide layer, and a metallic layer.

18. The multi-photon optical probe of claim 8, wherein the lateral scanning stage is positioned proximally to the distal optics and the axial scanning stage is positioned distally from the distal optics.

* * * * *